United States Patent
Tannoury et al.

(10) Patent No.: US 8,491,611 B2
(45) Date of Patent: Jul. 23, 2013

(54) NEURAL TISSUE RETRACTION AND PRESERVATION DEVICE

(75) Inventors: Tony Tannoury, Andover, MA (US);
Michael J O'Neil, Raynham, MA (US);
Derek Shaw, Raynham, MA (US);
Hassan Serhan, Raynham, MA (US)

(73) Assignee: DePuy Synthes Products, LLC., Raynham, MA (US)

( * ) Notice: Subject to any disclaimer, the term of this patent is extended or adjusted under 35 U.S.C. 154(b) by 406 days.

(21) Appl. No.: 12/641,476

(22) Filed: Dec. 18, 2009

(65) Prior Publication Data
US 2011/0152627 A1    Jun. 23, 2011

(51) Int. Cl.
*A61B 17/08* (2006.01)
(52) U.S. Cl.
USPC .......................................... 606/152
(58) Field of Classification Search
USPC ................ 606/139, 141, 142, 143, 151–153, 606/156–158, 75, 120, 219, 220, 221; 24/710.8, 24/710.9
See application file for complete search history.

(56) References Cited

U.S. PATENT DOCUMENTS

| | | | | |
|---|---|---|---|---|
| 3,403,428 A * | 10/1968 | Sheffer | ......................... | 24/710.8 |
| 4,217,902 A * | 8/1980 | March | ......................... | 606/221 |
| 4,997,436 A * | 3/1991 | Oberlander | .................. | 606/142 |
| 5,236,440 A * | 8/1993 | Hlavacek | ...................... | 606/219 |
| 6,814,742 B2 * | 11/2004 | Kimura et al. | ................ | 606/151 |
| 7,488,334 B2 * | 2/2009 | Jugenheimer et al. | ........ | 606/142 |
| 7,569,054 B2 | 8/2009 | Michelson | | |

OTHER PUBLICATIONS

Cloward, "A Self-Retaining Spinal Dural Retractor" J Neurosurg., Mar. 1952; 9(2):230-2.

* cited by examiner

*Primary Examiner* — Anu Ramana

(57) ABSTRACT

A self-retaining neural retraction clip, preferably having controlled retraction level and an off-set retraction means. This device can reduce operative site clutter to enhance disc access while providing consistent and stable dural retraction.

14 Claims, 7 Drawing Sheets

NEURAL TISSUE RETRACTION AND PRESERVATION DEVICE

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1β and TNF-α as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells within the disc (or invading macrophases) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices", or "interbody fusion devices".

Current spinal fusion procedures include approaches such as transforaminal lumbar interbody fusion (TLIF), posterior lumbar interbody fusion (PLIF), and extreme lateral interbody fusion (XLIF). TLIF and PLIF spinal fusion surgeries require refraction of neural tissues including the spinal cord and/or exiting nerve roots. Retraction is typically performed with hand held dural retractors that are manually placed and secured by an operative assistant who is standing on the contralateral side of the patient.

This position across from the surgeon greatly reduces visibility of the neural retraction for the operative assistant, increasing the risk of neural damage. Frequent adjustment of the retractor is required to ensure proper positioning, distance and the amount of dural retraction force applied. Significant patient risk, including dural tears, can be incurred if excessive retraction is applied or if the spinal cord is inadvertently released during the procedure.

In addition, the presence of the neural retractor crowds or obscures the surgical site, thereby minimizing visibility and access to the disc space for the operating surgeon.

Cloward, "A Self-Retaining Spinal Dural Retractor" *J. Neurosurg.*, 1952 March; 9(2):230-2, discloses a modified Hoen laminectomy retractor having a retraction spatula.

U.S. Pat. No. 7,569,054 (Michelson) discloses a tubular member having a passage and opposing bone penetrating extensions adapted to piece opposed vertebral bodies.

The objective of this device is to reduce operative site crowding to enhance disc access while providing for consistent and stable dural retraction.

SUMMARY OF THE INVENTION

The present inventors have developed a device and a method for neural tissue retraction for spinal surgery that overcomes the disadvantages associated with conventional spinal cord retraction.

In particular, the device is a self-retaining retractor clip. When used in spinal surgery, the self-retaining nature of the clip eliminates the need to continuously manually retract the neural structures.

Preferred devices of the present invention include a) a self-retaining neural retraction clip, b) a neural retraction clip with controlled refraction level, and c) a neural retraction clip with off-set retraction means.

Therefore, in accordance with the present invention, there is provided a neural tissue retractor comprising:
  a) first and second legs, each leg having an inner portion and a outer portion,
  b) a curved intermediate section connecting the inner portions of the first and second legs to provide (typically, spring-like) compression and expansion,
  c) first and second feet respectively extending from the outer portions of the first and second legs, each foot having a tooth adapted to pierce a vertebral body.

DETAILED DESCRIPTION OF THE INVENTION

Figure 1A:
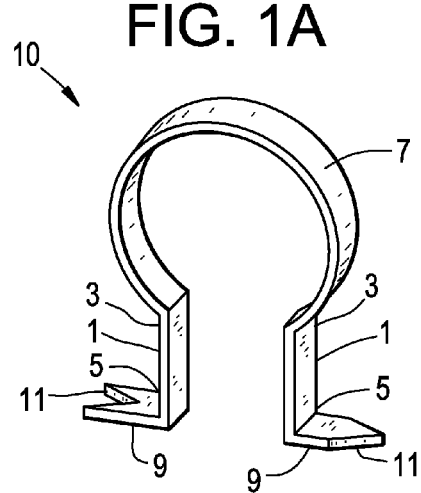
FIG. 1A-1C discloses various views of a self-retaining neural refraction clip of the present invention.
Figure 1B:
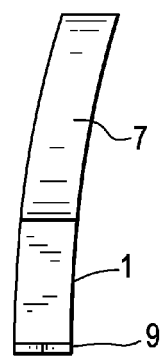
Figure 1C:
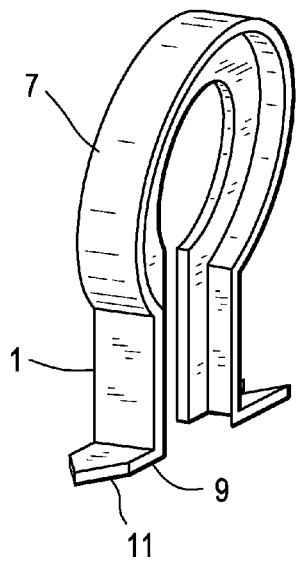

Now referring to FIGS. 1A-C, the self retaining neural retraction clip includes a spring clip having two attached feet. In use, the spinal cord is retracted, the clip is compressed and is placed between two adjacent vertebral bodies. Once the clip is in place, the compression is released so that the spiked feet pierce into and become seated within the endplate of each vertebral body. The spikes on the feet prevent clip rotation and ensure that the device maintains its position. The clip can have various geometries to minimize neural impingement.

Therefore, in accordance with the present invention, there is provided a neural tissue retractor 10 comprising:
a) first and second legs 1, each leg having an inner portion 3 and a outer portion 5,
b) a curved intermediate section 7 connecting the inner portions of the first and second legs to provide spring-like compression and expansion,
c) first and second feet 9 respectively extending from the outer portions of the first and second legs, each foot having a tooth 11 adapted to pierce a vertebral body.

In some embodiments, the curved intermediate portion comprises a portion of substantially a circle. Preferably, the portion of the circle defines an arc of at least about 270 degrees, more preferably at least 300 degrees.

In some embodiments, each foot has at least two teeth extending therefrom. Preferably, each foot extends substantially perpendicularly from its respective leg.

In some embodiments, the two legs of the present invention are substantially parallel to define a plane. In some embodiments, thereof, the curved intermediate portion lies substantially in the plane formed by the two legs. In other embodiments, the curved intermediate portion extends out of the plane formed by the two legs. This curve can lie in a multitude of planes. In some embodiments, (as in FIG. 1B), the extension of the curved intermediate portion out of the plane is due to an anterior-posterior curve in the curved intermediate portion. In other embodiments (as in FIGS. 3B and 4A), the extension of the curved intermediate portion out of the plane is due to a medial-lateral curve in the curved intermediate portion.

In some embodiments, the interior of the curved intermediate portion of the clip is substantially open (as in FIG. 1A). In others, the interior of the curved intermediate portion of the clip is at least 25% closed (as in FIG. 1C).

Also in accordance with the present invention, there is provided a method of preserving retraction of a neural tissue (such as a spinal cord), comprising the steps of:
a) retracting the neural tissue,
b) compressing a clip of the present invention,
c) placing the clip between two endplates of adjacent vertebral bodies so that each foot is substantially perpendicular to a respective vertebral body, and
d) releasing the compression upon the clip such that the spiked feet become seated into the endplate of each vertebral body.

Figure 1D:
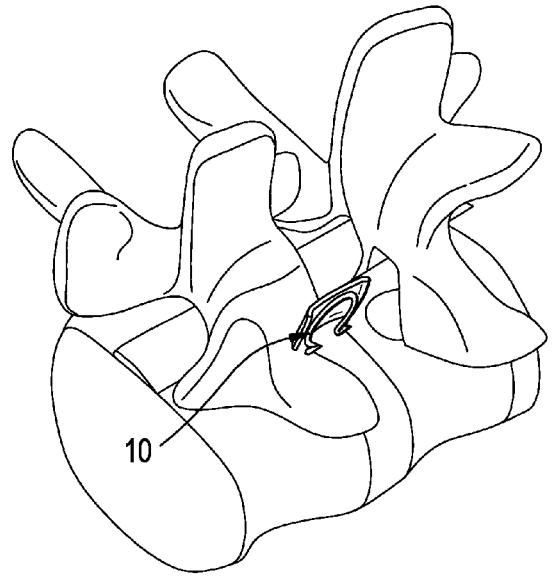
FIG. 1D discloses a neural retraction clip of the present invention retaining by opposing vertebrae.

FIG. 1D discloses the clip 10 attached in position in the spine.

Figure 2A:
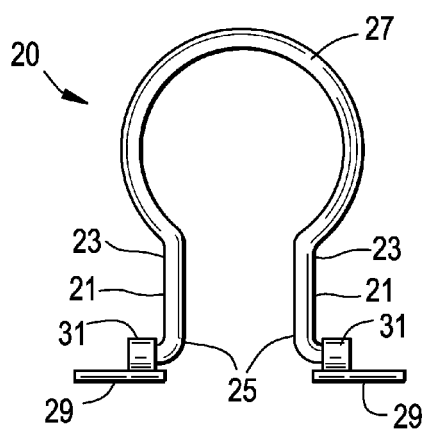
FIGS. 2A-C disclose the neural retraction clip of the present invention having a lock and key mechanism for controlling the degree of retraction.
Figure 2B:
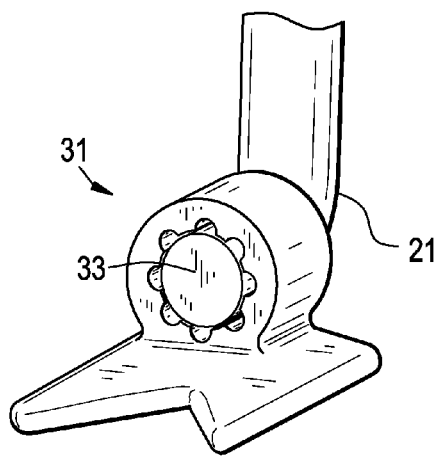
Figure 2C:
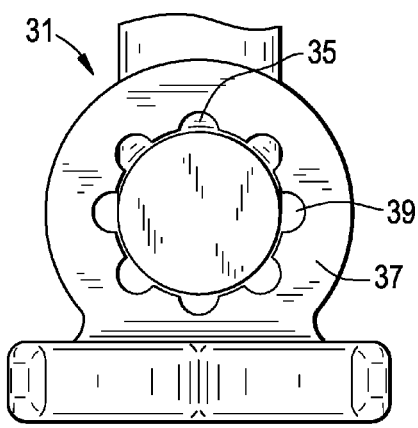

Now referring to FIGS. 2A-2C, the neural clip with controlled retraction level includes a self-retaining neural retraction clip along with rotatable retraction level and locking means. The adjustable retraction is accomplished with the use of a rotating key-based lock on the feet of the clip. In this case, the compressed clip is placed between the vertebral bodies and released such that the spiked feet are seated into each vertebral body. The clip is rotated to retract the cord. The keyway lock allows incremental rotation until the desired amount of spinal cord retraction is achieved.

Therefore, in accordance with the present invention, there is provided a neural tissue retractor 20 comprising:
a) first and second legs 21, each leg having an inner portion 23 and a outer portion 25,
b) a curved intermediate section 27 connecting the inner portions of the first and second legs to provide spring-like compression and expansion,
c) first and second feet 29 respectively extending from the outer portions of the first and second legs,
wherein each leg and its respective foot are connected by rotating lock and key connection 31.

In some embodiments (as in FIG. 2C), key of the lock and key mechanism is presented as a rod 33 having a plurality of spaced longitudinally oriented projections 35, while the corresponding lock 37 is presented as a tube having a plurality of mating longitudinal grooves 39.

In some embodiments (as in FIG. 2C), a rod 33 is formed by an extension of a leg 21, while the tube is formed as an extension of a foot. In others, a rod is formed by an extension of a foot, while the tube is formed as an extension of a leg.

Figure 2D:
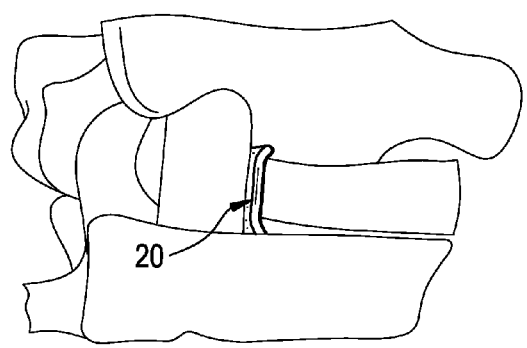
FIG. 2D shows the clip of FIGS. 2A-2C in its use location.

FIG. 2D discloses the clip 20 attached in position in the spine.

Figure 3A:
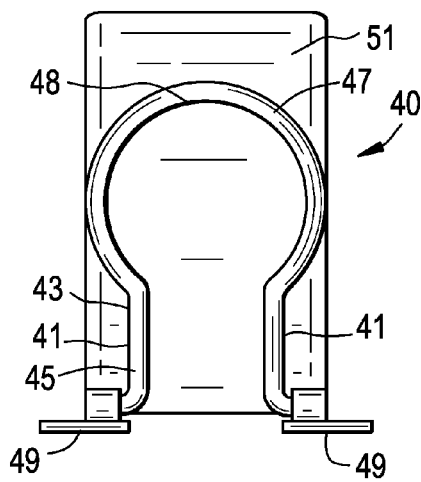
FIGS. 3A-3C discloses various views of a self-retaining neural retraction clip of the present invention having a retractor shield.
Figure 3B:
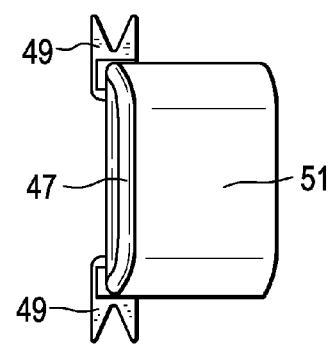
Figure 3C:
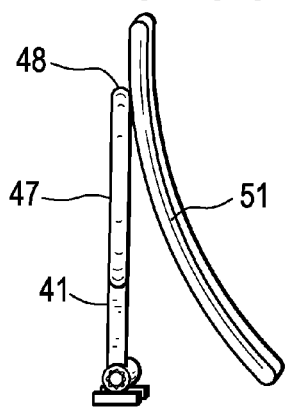

Now referring to FIGS. 3A-C, the neural clip with conformable off-set retraction means is very similar to the clip with controlled retraction, except the retractor blade is off-set from the attachment location allowing placement at varying distances from the spinal cord. The retraction shield geometry is designed with conforming radius in the medial-lateral and anterior-posterior planes to minimize impingement upon the spinal cord.

Therefore, in accordance with the present invention, there is provided a neural tissue retractor 40 comprising:
a) first and second legs 41, each leg having an inner portion 43 and a outer portion 45,
b) a curved intermediate section 47 connecting the inner portions of the first and second legs to provide spring-like compression and expansion,
c) first and second feet 49 respectively extending from the outer portions of the first and second legs,
d) a retractor shield 51 connected to the curved intermediate section.

In some embodiments, the retractor shield is curved. In some embodiments, the retractor shield is connected to the curved intermediate portion substantially at the apex 48 of the curved intermediate portion (i.e., the portion opposite the legs). In some embodiments, the shield is connected to the curved intermediate section to form a substantially V-shaped clip (as shown in FIG. 3C).

Figure 3D:
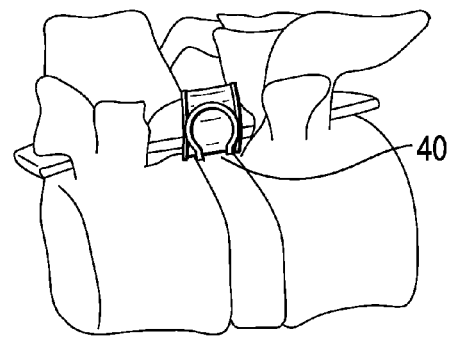
FIGS. 3D-F show the clip of FIGS. 3A-3Cc in its use location.
Figure 3E:
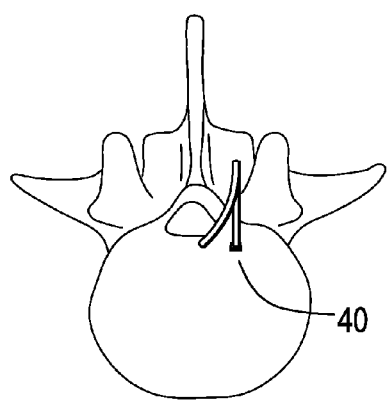
Figure 3F:
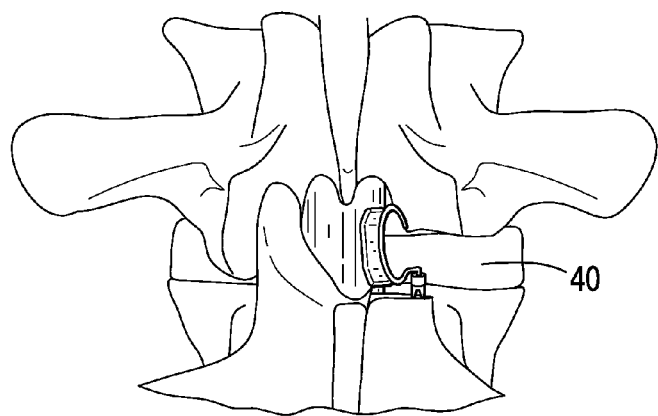

FIGS. 3D-F disclose the clip 40 attached in position in the spine.

In some embodiments, insertion of the clip of the present invention is accomplished by using clamping forceps to secure the legs of the clip and squeeze them into a compressed configuration. Now referring to FIG. 4B, in one preferred embodiment, each leg of the clip has a loop extending therefrom, and each arm 81 of the forceps 83 has a pin 85 adapted for reception in a loop. In use, each pin is inserted into a respective loop, and the forceps are squeezed to provide the desired level of leg compression.

Preferably, the inserter can be shielded to minimize inadvertent damage to soft tissue or neural tissue. Also preferably, the inserter device can be used to extract the clip from the patient after the operation is completed.

Figure 4A:
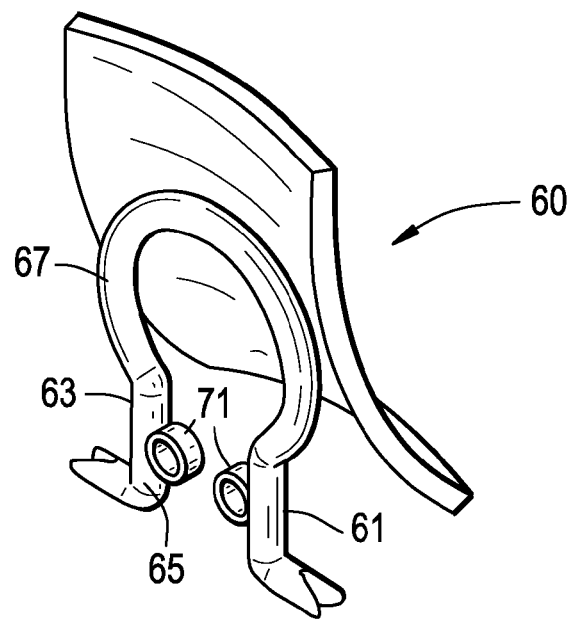
FIG. 4A discloses a self-retaining neural retraction clip of the present invention having loops for receiving inserter pins.
Figure 4B:
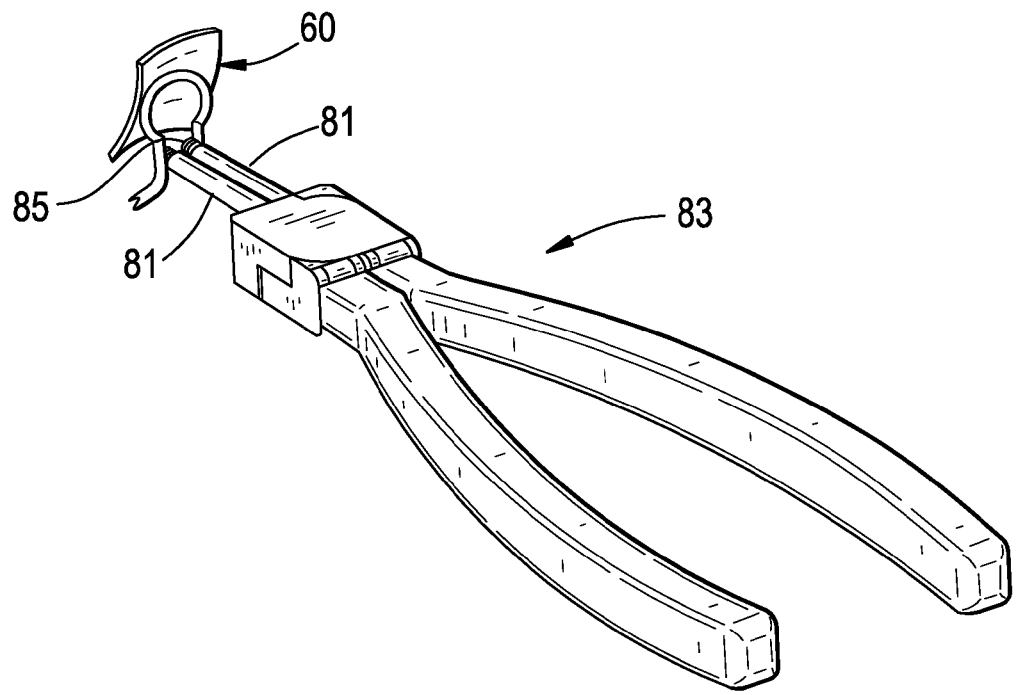
FIG. 4B shows the clip of FIG. 4A attached to an inserter.
Figure 4C:
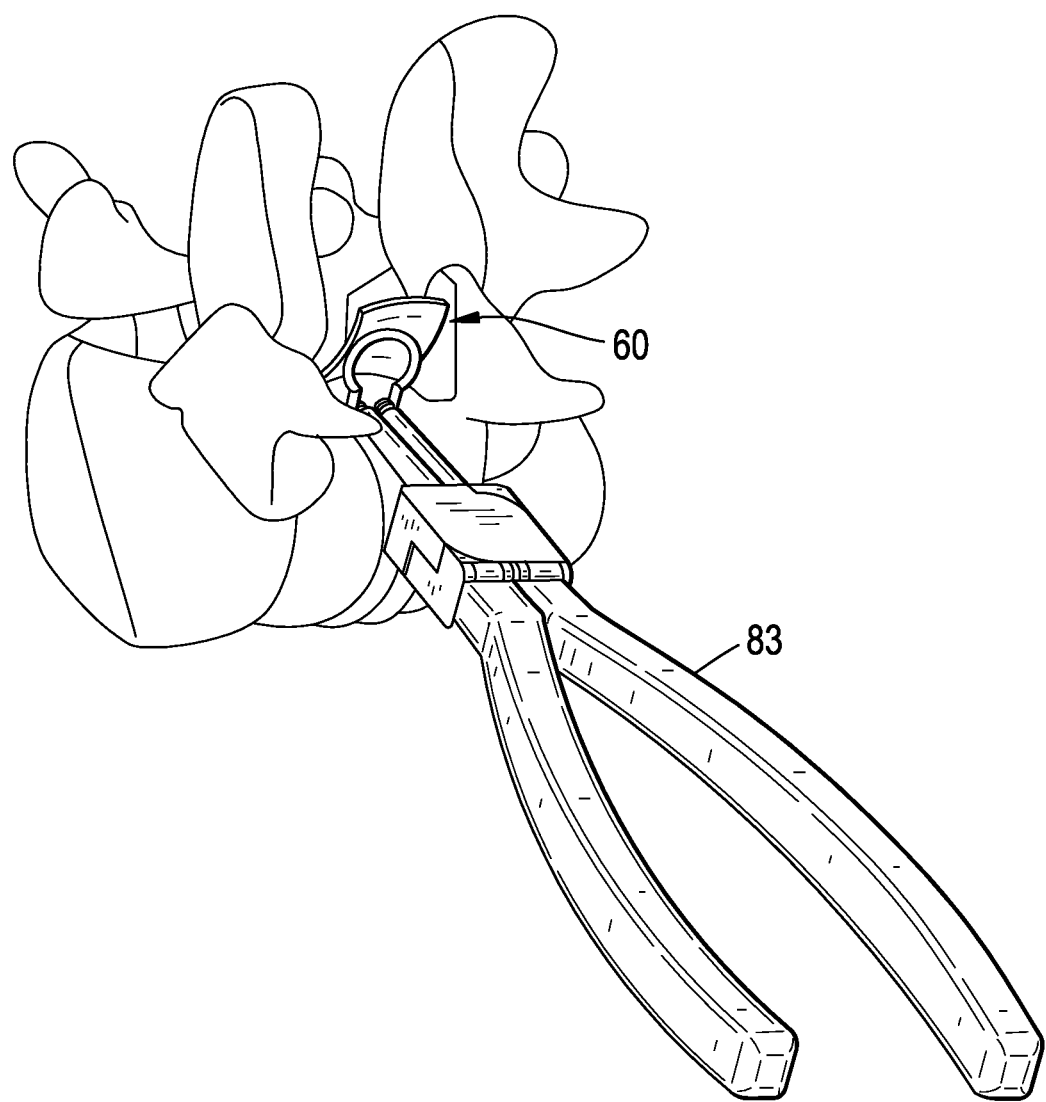
FIG. 4C discloses the assembly of FIG. 4B inserted between opposing vertebrae.

Therefore, now referring to FIGS. 4A-C, in accordance with the present invention, there is provided a neural tissue retractor 60 comprising:
a) first and second legs 61, each leg having an inner portion 63 and a outer portion 65, each leg having an inserter receptor 71 adapted for connection with an inserter,
b) a curved intermediate section 67 connecting the inner portions of the first and second legs to provide spring-like compression and expansion,
c) first and second feet 69 respectively extending from the outer portions of the first and second legs.

Preferably, the inserter receptor is a loop.

FIG. 4C discloses the clip 60 attached in position in the spine.

Figure 5A:
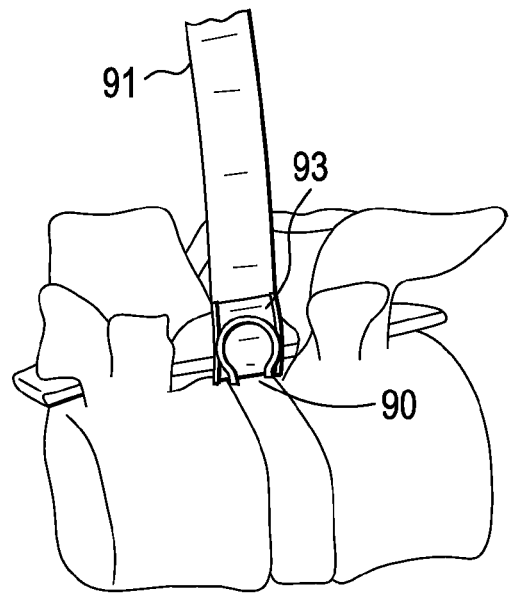
FIGS. 5A-B show an implanted clip of the present invention having tether attached thereto.
Figure 5B:
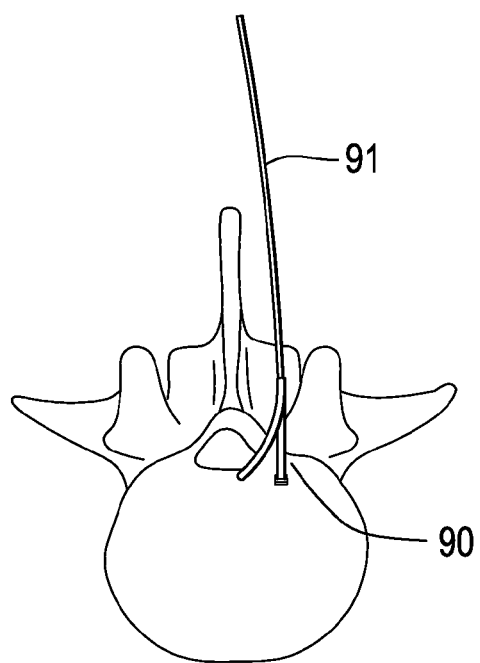

Now referring to FIGS. 5A-B, additional soft tissue retraction can be accomplished by pre-attaching the clip to a tether, securing the clip to bony structures, and then tensioning and securing the tether to either the patient, an external retraction system or the operating table.

Therefore, in some embodiments, the retractor clip 90 of the present invention has a tether 91 attached thereto. In some embodiments, the tether is attached to the shield 93. In some embodiments, the tether is attached to the curved intermediate portion. In some embodiments, the tether is attached to at least one leg.

Figure 6:
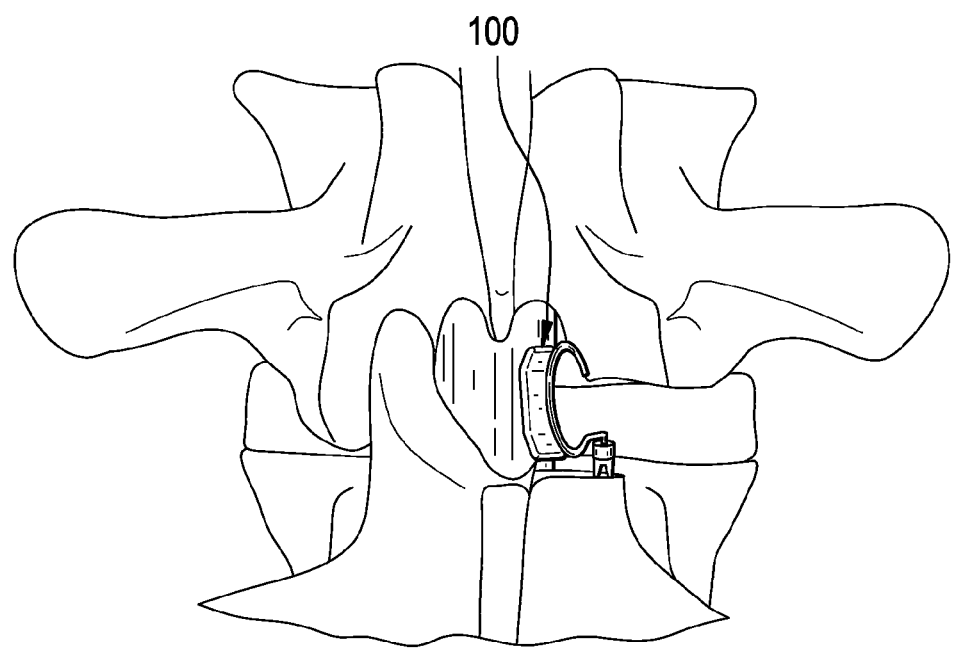
FIG. 6 shows a clip of the present invention attached to a lamina.

Now referring to FIG. 6, the clip 100 of the present invention can also be attached to other locations to distract neural tissues in a similar fashion. The alternate attachment locations are generally bony landmarks adjacent to the neural tissues. These landmarks include the lamina (as shown in FIG. 6), the pars, the facets, pedicles, and the spinous processes.

The neural retraction clip of the present invention can be produced from a variety of biocompatible metals or plastics. Suitable metals include stainless steel, titanium, nitinol or cobalt-chrome. Selection of these materials will allow the clip to be first squeezed to produce elastic compression for insertion and then released to produce expansion for vertebral body securement. A semi-rigid to rigid polymer with shape memory properties such as PEEK, polypropylene, polyethylene can also be utilized. These materials would allow multiple compression cycles without structural fatigue as well as radio-lucency to enable intra-operative imaging of the surgical site. Hybrid components can also be selected, and include producing the spikes and clip from TiN for expansion and the shield from a conformable polymer (like polypropylene) to maximize conformance to the neural tissues. The material selection can provide either elastic or plastic deformation.

We claim:

1. A neural tissue retractor comprising:
a) first and second legs, each leg having an inner portion and an outer portion,
b) a curved intermediate section connecting the inner portions of the first and second legs and having an apex,
c) a retractor shield connected at the apex of the curved intermediate section
first and second feet respectively extending from the outer portions of the first and second legs, each foot having a tooth adapted to pierce a vertebral body,
wherein the curved intermediate section provides spring-like expansion of the legs in response to compression,
wherein the curved intermediate section forms a first plane, and wherein the shield and curved intermediate section substantially form a V-shape in a second plane orthogonal to the first plane.

2. The retractor of claim 1 wherein the curved intermediate portion comprises a portion of a circle.

3. The retractor of claim 2 wherein the portion of the circle defines an arc of at least about 270 degrees.

4. The retractor of claim 1 wherein each foot has at least two teeth extending therefrom.

5. The retractor of claim 1 wherein each foot extends substantially perpendicularly from its respective leg.

6. The retractor of claim 1 wherein the two legs are substantially parallel to each other to substantially define a third plane.

7. The refractor of claim 6 wherein the curved intermediate portion lies substantially in the third plane formed by the two legs.

8. The retractor of claim 1 wherein a region bounded by the curved intermediate portion of the clip is substantially open.

9. The retractor of claim 1 wherein a region bounded by the curved intermediate portion of the clip is at least 25% closed.

10. A neural tissue retractor comprising:
a) first and second legs, each leg having an inner portion and a outer portion,
b) a curved intermediate section connecting the inner portions of the first and second legs to provide compression and expansion,
c) first and second feet respectively extending from the outer portions of the first and second legs,
wherein each leg and its respective foot are connected by a rotating lock and key connection,
wherein the key of the lock and key mechanism is presented as a rod having a plurality of spaced longitudinally oriented projections, and the lock is presented as a tube having a plurality of mating longitudinal grooves.

11. The retractor of claim 10 wherein the rod is formed as an extension of one of the legs, and the tube is formed as an extension of one of the feet.

12. The retractor of claim 10 wherein the rod is formed by an extension of one of the feet, and the tube is formed as an extension of one of the legs.

13. A method of preserving refraction of a neural tissue, comprising the steps of:
a) retracting the spinal cord,
b) compressing a clip comprising:
i) first and second legs, each leg having an inner portion and an outer portion,
ii) a curved intermediate section connecting the inner portions of the first and second legs and having an apex,
iii) a retractor shield connected at the apex of the curved intermediate section,
first and second feet respectively extending from the outer portions of the first and second legs, each foot having a tooth adapted to pierce a vertebral body,
wherein the curved intermediate section provides spring-like expansion of the legs in response to compression,
c) placing the clip between endplates of adjacent first and second vertebral bodies so that each foot is substantially perpendicular to a respective vertebral body, and
d) releasing the compression upon the clip such that the first spiked foot becomes seated into the endplate of the first vertebral body and the second spiked foot becomes seated into the endplate of the second vertebral body.

14. A neural tissue retractor comprising:
a) first and second legs, each leg having an inner portion and a outer portion, each leg having an inserter receptor adapted for connection with an inserter
b) a curved intermediate section connecting the inner portions of the first and second legs to provide compression and expansion, c) first and second feet respectively extending from the outer portions of the first and second legs, the feet extending away from each other, wherein the curved intermediate section provides spring-like expansion of the legs in response to compression, wherein the inserter receptor is a loop.

\* \* \* \* \*